United States Patent [19]

Agarwal

[11] Patent Number: 5,018,086
[45] Date of Patent: May 21, 1991

[54] FAULT DETECTION IN OLEFIN OXIDATION REACTOR

[75] Inventor: Suresh C. Agarwal, Euclid, Ohio

[73] Assignee: The Babcock & Wilcox Company, New Orleans, La.

[21] Appl. No.: 440,930

[22] Filed: Nov. 12, 1982

Related U.S. Application Data

[63] Continuation-in-part of Ser. No. 370,703, Apr. 22, 1982, Pat. No. 4,488,239.

[51] Int. Cl.$^5$ .............................................. G06F 15/46
[52] U.S. Cl. ..................................... 364/557; 364/496
[58] Field of Search ............... 364/496, 499, 500–503, 364/557; 203/1; 422/62, 105, 108, 110; 585/263, 401, 501, 950, 951

[56] References Cited

U.S. PATENT DOCUMENTS

| | | | |
|---|---|---|---|
| 2,908,734 | 10/1959 | Cottle | 585/501 |
| 2,974,017 | 3/1961 | Morgan | 585/501 |
| 3,070,302 | 12/1962 | Fluegel et al. | 364/496 |
| 3,080,219 | 3/1963 | Harvey, Jr. | 585/501 |
| 3,275,809 | 9/1966 | Tolin et al. | 364/500 |
| 3,676,653 | 7/1972 | Arens et al. | 364/496 |
| 4,132,530 | 1/1979 | Schwimmer | 364/500 |
| 4,187,542 | 2/1980 | Ball et al. | 364/502 |
| 4,241,230 | 12/1980 | Drinkard | 585/263 |
| 4,249,907 | 2/1981 | Callejas | 364/500 |
| 4,249,908 | 2/1981 | Funk | 364/500 |

Primary Examiner—Gary V. Harkcom
Assistant Examiner—Dale M. Shaw
Attorney, Agent, or Firm—Vytas R. Matas; Robert J. Edwards

[57] ABSTRACT

A method and apparatus for determining heat transfer effectiveness comprises measuring coolant flow rate and input temperature for coolant to the reactor, utilizing temperature values for reactant and effluent temperatures in a relationship to obtain a value for the log means temperature difference across the reactor and calculating the actual heat transfer coefficient for heat transfer surfaces of the reactor as a function of the log mean temperature difference, the heat transfer area, the coolant flow rate and additional constant factors which are characteristics of the coolant itself.

3 Claims, 3 Drawing Sheets

FAULT DETECTION IN OLEFIN OXIDATION REACTOR

CROSS-REFERENCE TO RELATED APPLICATION

This is a continuation-in-part of a previous application entitled TEMPERATURE CONTROL SYSTEM FOR OLEFIN OXIDATION REACTOR having Ser. No 06/370 703 filed on Apr. 22, 1982, now U.S. Pat. No. 4,488,239 issued Dec. 11, 1984, to the same inventor as the present application.

Additional relevant information concerning the present application can also be found in another continuation-in-part application of the aforementioned parent application entitled OLEFIN OXIDATION REACTOR TEMPERATURE CONTROL, having Ser. No. 06/375,795 filed on May 7, 1982, U.S. Pat. No. 4,491,924 and also to the same inventor as the present application.

FIELD AND BACKGROUND OF THE INVENTION

The present invention relates, in general, to control equipment and techniques for chemical reactors and, in particular, a new and useful apparatus and method of measuring heat transfer effectiveness in an olefin oxidation reactor. If the heat transfer effectiveness falls below a selected level, an unsafe or undesirable condition exists so that a measurement of the heat transfer effectiveness can be utilized for fault detection in the reactor.

In an olefin, in particular, ethylene oxide manufacturing process, ethylene and oxygen or air are mixed and fed to an isothermal multitubular reactor. Ethylene is oxidized into ethylene oxide in the presence of a catalyst. Carbon dioxide and water are produced as by-products.

The aforementioned related applications disclose control schemes for controlling reactor temperature for the exothermic oxidation reaction. This is done by manipulating the flow rate of coolant based on a maximum and minimum reactor temperature, heat of reaction and percent oxidation, among other parameters.

During the normal course of heat removal, reactor surfaces become fouled due to the deposition of scale resulting from impurities present in the coolant. This causes changes in the thermal properties of the reactor on the coolant side thereof.

As a consequence, either coolant flow rate must be increased or the surfaces must be cleansed by chemical or manual means. In the absence of these corrective steps, reactor temperature would increase because of a reduced overall heat transfer coefficient. This would result in increased olefin oxidation to by-products, that is, carbon dioxide and water, increased probability of catalyst poisoning and potential reactor operation in an unsafe region due to the larger heat of reaction of the exothermic side reactions.

SUMMARY OF THE INVENTION

According to the invention, it is considered essential that heat transfer effectiveness be measured and that the results be made available to the reactor control system and plant operating personnel so that corrective actions can be taken. Accordingly, it is important that the measurement be made "on line" so that a real time measurement of heat transfer effectiveness is provided.

Accordingly, an object of the present invention is to provide a method of determining the heat transfer effectiveness of a reactor for containing a reaction and having coolant supply means for supplying a coolant to the reactor, reactant supply means for supplying a reactant to the reactor in heat transfer relationship with the coolant over a heat transfer area, and effluent discharge means for discharging an effluent from the reactor, comprising, measuring the coolant flow rate to the reactor, providing values corresponding to the heat of vaporization, the boiling temperature and the specific heat of the coolant, measuring the inlet temperature of the coolant to the reactor, determining the log mean temperature difference over the reactor, and calculating the heat transfer effectiveness according to the equation $$U = \frac{F_c}{A\Delta T_m} [C_{pc}(T_{c2} - T_{c1}) + \lambda]$$

Another object of the present invention is to provide an apparatus for determining the heat transfer effectiveness of the reactor according to the foregoing method.

A still further object of the invention is to provide such a method and apparatus wherein the log mean temperature difference is determined as a function of the reactant temperature entering the reactor, the effluent temperature leaving the reactor, the reaction temperature, the coolant boiling temperature and the coolant inlet temperature.

A still further object of the invention is to provide such a method and apparatus wherein reaction temperature is obtained by measuring a plurality of temperatures along the height of the reactor, finding a maximum of all the temperatures measured along the height of the reactor, finding a minimum of all the temperatures measured along the height of the reactor and obtaining a value between the maximum and minimum temperatures which corresponds to the reaction temperature.

A further object of the invention is to provide an apparatus for determining the heat transfer effectiveness of a reactor, in particular a reactor for containing an exothermic olefin oxidation reaction, which is simple in design, rugged in construction and economical to manufacture.

For an understanding of the principles of the invention, reference is made to the following description of typical embodiments thereof as illustrated in the accompanying drawings.

DESCRIPTION OF THE PREFERRED EMBODIMENTS

Figure 1:
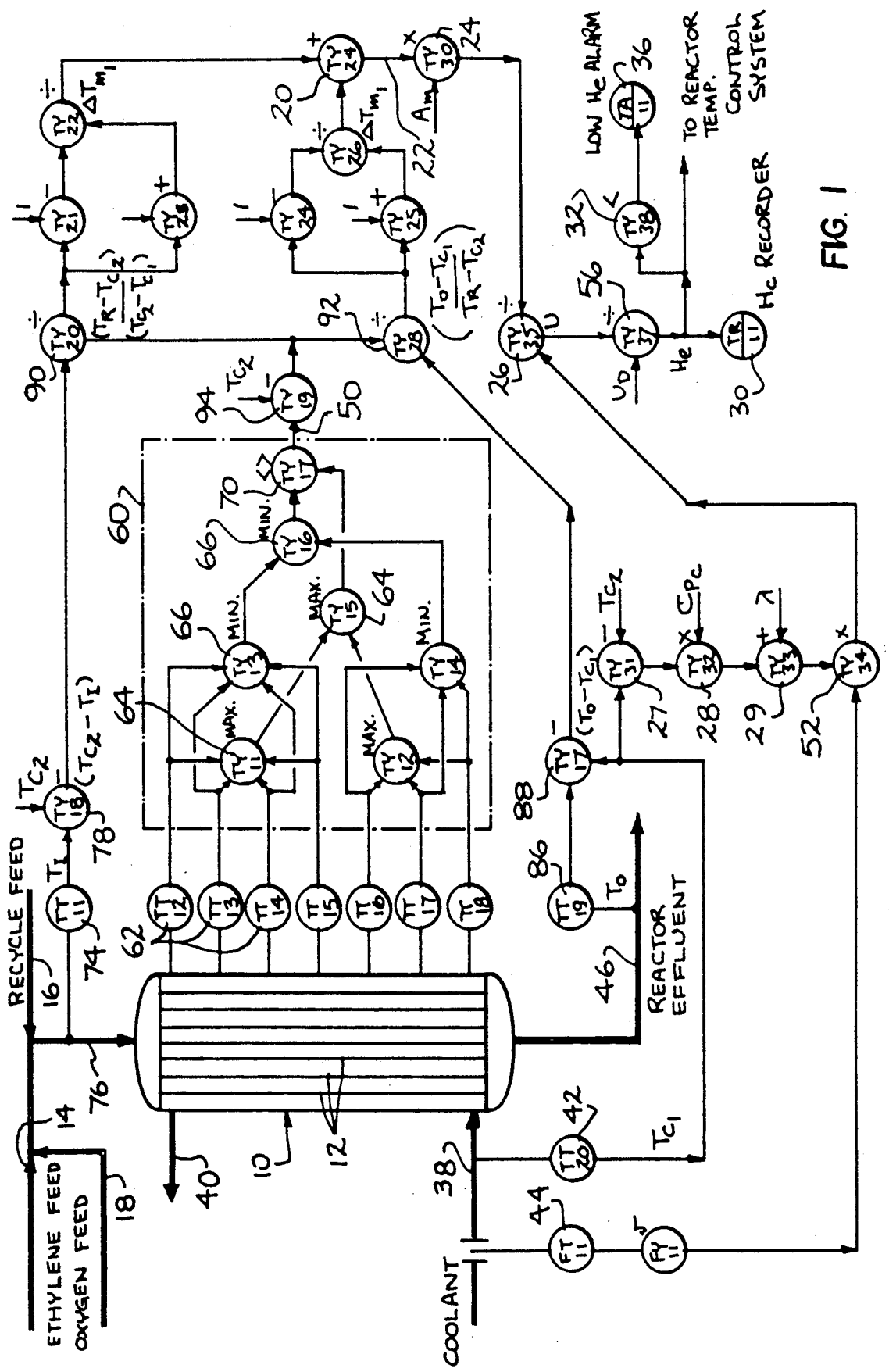
FIG. 1 is a schematic representation of an apparatus according to the invention.
Figure 2:
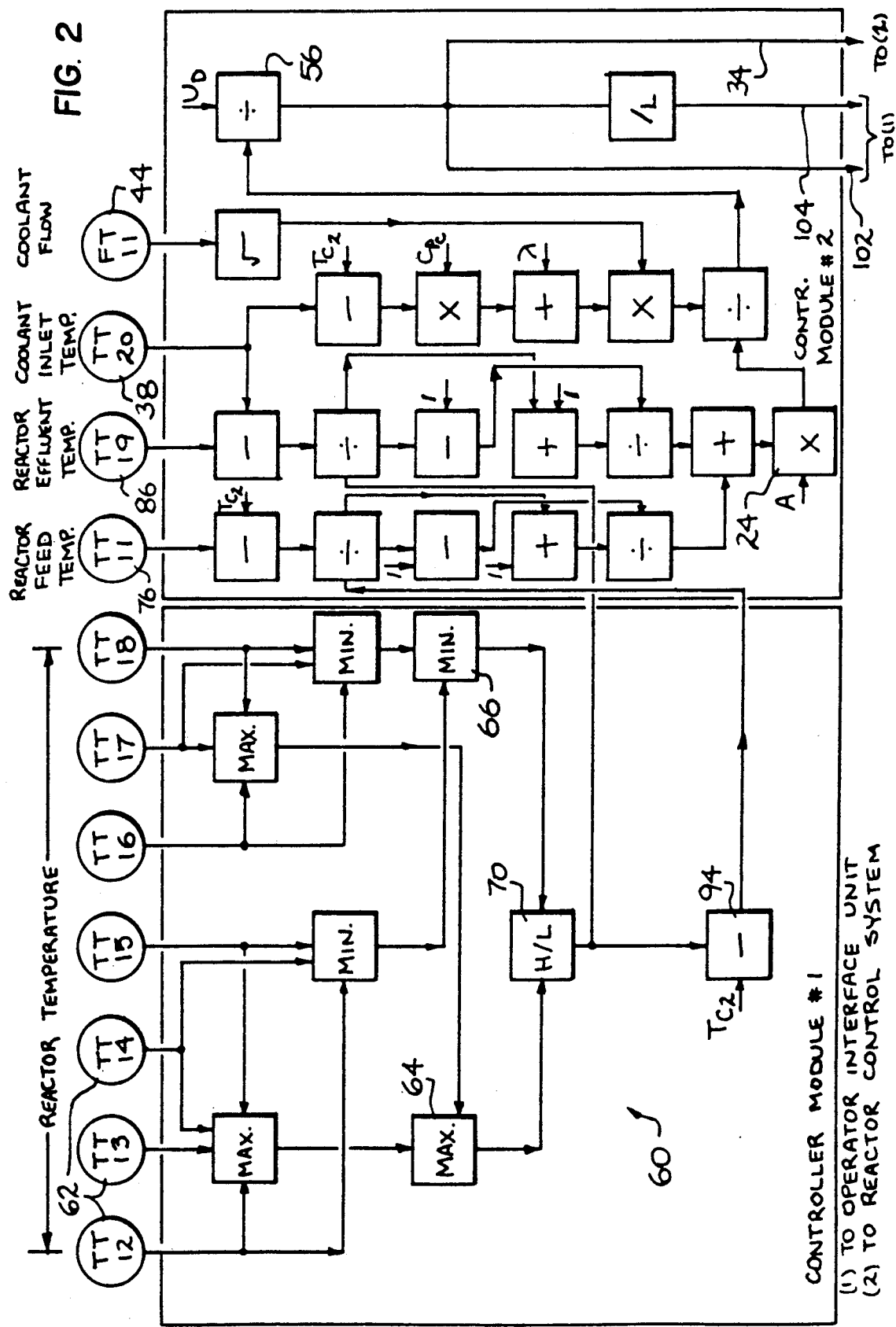
FIG. 2 is a schematic representation of another embodiment of the invention.

FIGS. 1 and 2 of the drawings illustrate two separate systems that can be utilized to implement the invention.

Before discussing this apparatus specifically, however, the insights and reasoning used in achieving the invention are first set forth.

In the following analysis let:

$C_{pc}$ = specific heat of the coolant to the reactor;

$F_c$ = Actual coolant flow rate;
$\lambda$ = Heat of vaporization of the coolant;
$T_{cl}$ = Inlet temperature of the coolant; and
$T_{c2}$ = Boiling temperature of the coolant.
Thus, total heat removed is given by:

$$Q_R = F_c C_p (T_{c2} - T_{di\,cl}) + F_c \lambda \tag{1}$$

Also:

$$Q_R = UA\Delta T_m \tag{2}$$

where: $Q_R$ = Total heat rate;
$U$ = Overall heat transfer coefficient;
$\Delta T_m$ = Log mean temperature difference; and
$A$ = Heat transfer area in the reactor.

Heat transfer area A is a fixed value which is available from the design data for the reactor. Inlet and outlet temperatures are measured for calculating $\Delta T_m$. Boiling temperature $T_{c2}$ is not measured as it is known from the fluid coolant characteristics.

From equations (1) and (2), there arises the equation:

$$U = \frac{F_c}{A\Delta T_m} [C_p(T_{c2} - T_{c1}) + \lambda] \tag{3}$$

This expression gives the actual heat transfer coefficient for the reactor.

Letting $U_D$ be the overall heat transfer coefficient by reactor design, then overall heat transfer effectiveness can be defined as:

$$H_e = \frac{U}{U_D} \tag{4}$$

When the heat transfer surface is clean that is, no fouling exists, then $U_D = U$, and $He = 1$, otherwise $0 \leq H_e < 1$.

Thus, by evaluating the value of $H_e$ only, the actual heat transfer effectiveness can be found, and can be used for (a) compensating coolant flow rate, (b) generating an alarm for operator information, and (c) use of this signal in the reactor shutdown and emergency control systems.

Figure 3:
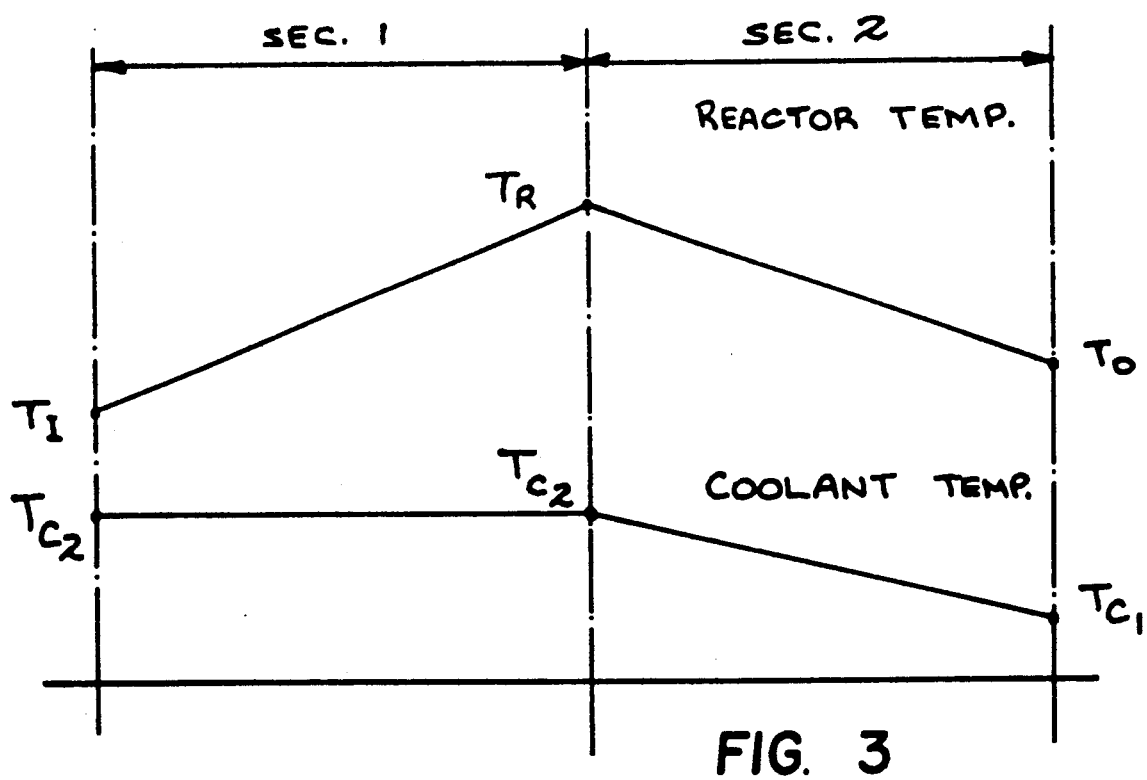
FIG. 3 is a graph which illustrates a temperature profile for a reaction in the reactor.

On the reaction side, the temperature profile consists of (a) reaction products at the reaction temperature and (b) cooling of reactor effluent mixture to exit temperature. Consequently, standard methodology for calculation of log mean temperature difference ($\Delta T_m$) is not applicable directly. The following method is used:

Graphically, temperature profiles may be represented as shown in FIG. 3. Overall log mean temperature difference is thus:

$$\Delta T_m = \Delta T_{m1} + \Delta T_{m2} \tag{5}$$

where:

$\Delta T_{m1}$ = log mean temperature difference for section 1; and
$\Delta T_{ms}$ = log mean temperature difference for section 2.

Using a known relationship for $T_{m1}$:

$$\Delta T_{m1} = \frac{(T_R - T_{c2}) - (T_{c2} - T_I)}{\ln\left(\frac{T_R - T_{c2}}{T_{c2} - T_I}\right)} \tag{6}$$

where:
$T_I$ = reaction mixture feed temperature.

By using first order Padé approximation, the equation becomes:

$$\Delta T_{m1} = 2\left[\frac{1 - (T_R - T_{c2})/(T_{c2} - T_I)}{1 + (T_R - T_{c2})/(T_{c2} - T_I)}\right] \tag{7}$$

Similarly:

$$\Delta T_{m2} = 2\left[\frac{1 - (T_o - T_{c1})/(T_R - T_{c2})}{1 + (T_o - T_{c1})/(T_R - T_{c2})}\right] \tag{8}$$

where:
$T_o$ = reactor effluent temperature.

Thus, $\Delta T_m$ in equation (3) can be easily calculated from equations (5), (7) and (8).

An embodiment of the invention is shown in FIG. 1, using conventional electronic instrument and control components. The invention, however, can be easily and naturally implemented in a control computer system as well.

Referring to FIG. 1, reaction temperature $T_R$ is determined from reactor temperature sensor 62 via maximum-minimum logic means 60 and total log means temperature difference $\Delta T_m$ is calculated. Thereafter, the actual heat transfer coefficient is calculated from the measured coolant flow rate coolant inlet temperature, reactor feed and effluent temperature. Finally, heat transfer effectiveness is calculated. The value of this signal is displayed as a trend on a recorder 30, and checked for low level alarm at 32. Also, this signal is available for use in the reactor control system over line 34. Alarm 36 is activated to indicate low level of heat transfer effectiveness and thus a fault in the system.

Bailey 1000 Electronic Analog Instrumentation can be used throughout to provide the measurement of heat transfer effectiveness in the ethylene oxidate reactor. However, a microprocessor based NETWORK 90™ Control Computer can also be used for control, alarm, calculation and operator interface.

FIG. 2, illustrates an application of the invention with the use of a Network 90 ™ Controller Module, product specification E93-906. Operator interface may be provided with digital control stations, produce specification E93-902, which are dedicated panel board devices or by a CRT based Operator Interface Unit, Product specification E93-901, at lines 102 and 104.

Turning once more to FIG. 1, the invention embodied therein comprises a system for measuring heat effectiveness of a tubular reactor generally designated 10 having tubes 11 for the passage of ethylene plus oxygen as a reactant. The reactor is particularly adapted to oxidize ethylene into ethylene oxide with carbon dioxide and water as by-products in the effluent.

Ethylene is provided over line 14, with recycled ethylene being provided over line 16. Oxygen or air is provided over line 18. Reactant inlet line 76 provided with a temperature transmitter 74 supplies the reactant to the reactor 10 and the effluent is discharged over line 76 which has a temperature transmitter 86 for measuring the effluent temperature.

Coolant is supplied over line 38 and is discharged over line 40. Temperature transmitter 42 and flow transmitter 44 provide respective temperature and flow values for the coolant fed into reactor 10.

The maximum and minimum temperatures within the reactor are determined using temperature sensing means generally designated 60. Temperature sensing means 60 comprises a plurality of individual or banks of temperature sensors 63 which are distributed along the length of reactor 10. Elements 64 are utilized to determine the maximum temperature among temperature sensors 62 and elements 66 are utilized to determine the minimum temperature along these sensors. Values for minimum and maximum temperature are applied to element 72, to yield the reaction temperature $T_R$ which appears on line 50.

Temperature sensor 74 supplies a value corresponding to the reactant input temperature to subtraction unit 78 which subtracts this quantity from the boiling temperature $T_{c2}$.

The effluent temperature $C_o$ is provided by transmitter 86 to a subtraction unit 88 which subtracts the coolant input temperature $T_{c1}$ therefrom. Subtraction element 94 effects the subtraction of the coolant boiling temperature from the reaction temperature. Division elements 90 and 92 cooperate with subtraction element 94 to respectively generate major terms in equations (7) and (8) above.

These equations are completed in the logic elements to the right of division elements 90 and 92 which each have the function shown and cooperate with a final addition element 20 to generate, on line 22, the log mean temperature difference $\Delta T_m$. This is multiplied by the heat transfer area A by multiplication element 24 and supplied to division element 26.

The constant factors corresponding respectively to coolant boiling temperature, coolant specific heat and coolant heat of vaporization are factored in by subtraction, multiplication, and addition elements 27, 28 and 29. These elements cooperate with a multiplication unit 52 which factors in the coolant flow value and cooperates with division element 26 to complete equation (3) above.

The overall heat transfer effectiveness $H_e$ is determined and applied to line 34 by division elements 56 that factor in the design temperature efficient $U_D$. Referring to FIG. 2, the same function can be achieved utilizing the NETWORK 90 circuitry. Specifically, control module 1 and control module 2 are utilized as shown in FIG. 2 to achieve the various mathematical and logic functions. Similar parts are those having similar functions are designated with the same numerals as in FIG. 2. Since the functioning is the same, no additional details are provided for FIG. 2.

While specific embodiments of the invention have been shown and described in detail to illustrate the application of the principles of the invention, it will be understood that the invention may be embodied otherwise without departing from such principles.

What is claimed is:

1. An alarm system for a reactor for containing a reaction and having coolant supply means for supplying coolant to the reactor, the reactant supply means for supplying reactant to the reactor in heat transfer relationship with the coolant over a heat transfer area (A) and effluent discharge means for discharging effluent from the reactor, comprising:

coolant flow rate means for measuring the flow rate of coolant ($F_c$) to the reactor;

means for providing values corresponding to the heat of vaporization ($\lambda$) the boiling temperature ($T_{c2}$) and the specific heat ($C_{pc}$) of the coolant;

inlet temperature measuring means for measuring the inlet temperature ($T_{c1}$) of the coolant to the reactor;

means for determining the log mean temperature difference ($\Delta T_m$) across the reactor; and circuit means for calculating the actual heat transfer coefficient (U) of the heat transfer area according to the relationship:

$$U = \frac{F_c}{A \Delta T_m} [C_{pc}(T_{c2} - T_{c1}) + \lambda]$$

means for providing a value corresponding to a desired design heat transfer coefficient ($U_D$), said circuit including means for establishing a heat transfer effectiveness ($H_e$) of the reactor according to the relationship:

$$H_e = U/U_D;$$

comparison means connected to said circuit for comparing a calculated actual heat transfer effectiveness to a lower limit for heat transfer effectiveness of the reactor below which a fault exists; and alarm means connected to said comparator means for activating an alarm when the actual heat transfer effectiveness falls below the lower limit therefor.

2. An apparatus according to claim 1, wherein said means for determining the log mean temperature difference comprises reaction temperature means connected to the reactor for determining the reaction temperature ($T_R$), reactant inlet temperature means for measuring the inlet temperature ($T_I$) of the reactant, effluent temperature means for measuring the effluent temperature ($T_o$) leaving the reactor and a further circuit for calculating the log mean temperature difference according to the relationship.

$$\Delta T_m = 2 \left[ \frac{1 - (T_R - T_{c2})/(T_{c2} - T_I)}{1 + (T_R - T_{c2})/(T_{c2} - T_I)} \right] + 2 \left[ \frac{1 - (T_o - T_{c1})/(T_R - T_{c2})}{1 + (T_o - T_{c1})/(T_R - T_{c2})} \right].$$

3. An apparatus according to claim 2, wherein said further circuit includes a plurality of temperature transmitters connected at spaced locations along a length of the reactor, maximum temperature means connected to each of the temperature transmitters for establishing maximum temperature measured thereby, minimum circuit means connected to each of said temperature transmitters for establishing the minimum temperature measured thereby and reaction temperature means connected to said minimum and maximum circuit means for establishing a reaction temperature between said minimum and maximum temperatures.

* * * * *